United States Patent [19]
Pratt et al.

[11] Patent Number: 5,888,205
[45] Date of Patent: Mar. 30, 1999

[54] DEVICE FOR SEALING ACETABULAR CUP HOLES

[75] Inventors: Clyde Pratt, Somis; Albert Burdulis, San Francisco; Roger Carignan, Camarillo, all of Calif.

[73] Assignee: Kinamed, Inc., Newbury Park, Calif.

[21] Appl. No.: 732,646

[22] Filed: Oct. 1, 1996

[51] Int. Cl.⁶ ....................... A61F 2/34
[52] U.S. Cl. ........................... 623/23
[58] Field of Search ..................... 623/22, 23

[56] References Cited

U.S. PATENT DOCUMENTS

| | | | |
|---|---|---|---|
| 5,041,141 | 8/1991 | Ypma et al. | 623/22 |
| 5,314,487 | 5/1994 | Schryver et al. | 623/22 |
| 5,571,198 | 11/1996 | Drucker et al. | 623/22 |

OTHER PUBLICATIONS

Kinamed ATH System; The Exact–Fit Factor; Surgical Technique Reference Chart.

*Primary Examiner*—John G. Weiss
*Assistant Examiner*—John M. Black
*Attorney, Agent, or Firm*—Oppenheimer Wolff & Donnelly LLP

[57] ABSTRACT

The metal shell of an acetabular cup has holes that allow a surgeon to screw the shell to pelvic bone. To prevent the debris of ultra-high molecular weight polyethylene ("UHMWPE") or other plastic liner in the shell from migrating through the holes, the present invention seals each screw-receiving hole with a thin UHMWPE disc. The disc snaps into an annular groove in the hole. With the disc in place, debris from the liner does not pass through the screw holes.

8 Claims, 1 Drawing Sheet

DEVICE FOR SEALING ACETABULAR CUP HOLES

BACKGROUND OF THE INVENTION

1. Field of the Invention

The present invention is a medical device. In particular it is a device for sealing the screw holes in an acetabular cup.

2. State of the Art

Total hip replacement often requires replacement of a patient's acetabulum with an acetabular cup prosthesis. Acetabular reamers remove pelvic bone to create a properly sized region on the pelvis to receive the acetabular cup and liner. Typically, a surgeon uses hemispherical reamers until a chosen acetabular cup-receiving shell can seat. One such shell is part of the ATH System of Kinamed, Inc. of Newbury Park, Calif., assignee of this application. In some patients, the shell can be cemented to the pelvic bone, in others it may be press fit, however, many patients have insufficient bone to secure the shell. For those latter patients, the shell is screwed into the pelvis through screw holes in the shell.

Orthopedic surgeons have become concerned about the impact of ultra-high molecular weight polyethylene (UHMWPE) wear debris that may cause osteolytic changes within the patient's bone. It is thought that the screw holes may allow the potentially destructive particles to come into contact with bone and cause damage by virtue of the cellular reaction to the wear debris material.

SUMMARY OF THE INVENTION

It is an object of the present invention to disclose and provide an acetabular cup that avoids having UHMWPE wear debris pass through the screw-receiving holes of an acetabular cup. Specifically, the present invention seals each screw-receiving hole with a thin UHMWPE disc. The disc snaps into an annular groove in the hole. With the disc in place, material from the cup does not pass through the screw holes.

These and other objects of the invention may be seen more clearly from the detailed description of the preferred embodiment that follows.

DETAILED DESCRIPTION OF THE PREFERRED EMBODIMENTS

An acetabular cup replacement usually is required in total hip replacement surgery. Such cups usually have several parts including an outer metallic shell and a UHMWPE liner. Surgeons choose the proper shell and liner to accommodate different patients' needs.

Kinamed, Inc. publishes the "Kinamed ATH System," which describes parts pf the surgical procedure that this invention uses. The surgeon uses acetabular reamers to create the properly sized region on the pelvis to receive the acetabular cup. The typical reaming tool is hemispherical. Reaming begins through the articular cartilage and into the subchondral bone. If the patient's acetabular ridge is present, the surgeon uses it as a reference for anatomical positioning and reaming direction. The surgeon uses progressively larger reamers to continue exposing the cancellous bone bed as necessary. Reaming continues only until a chosen shell, which will receive the acetabular cup, can seat. The ATH shell is a low profile shell that is less of a hemisphere than the reamer.

The surgeon can check the size, shape and orientation of the reamed cavity by removing the reamer and inserting a trial shell of the same size of the reamer. However, for a correct and stable interference fit, the surgeon generally will choose a shell that is 2 mm larger than the final reamer used. Shells come in different sizes, and the shell shown and described in the exemplary embodiment is only one size.

Figure 1:
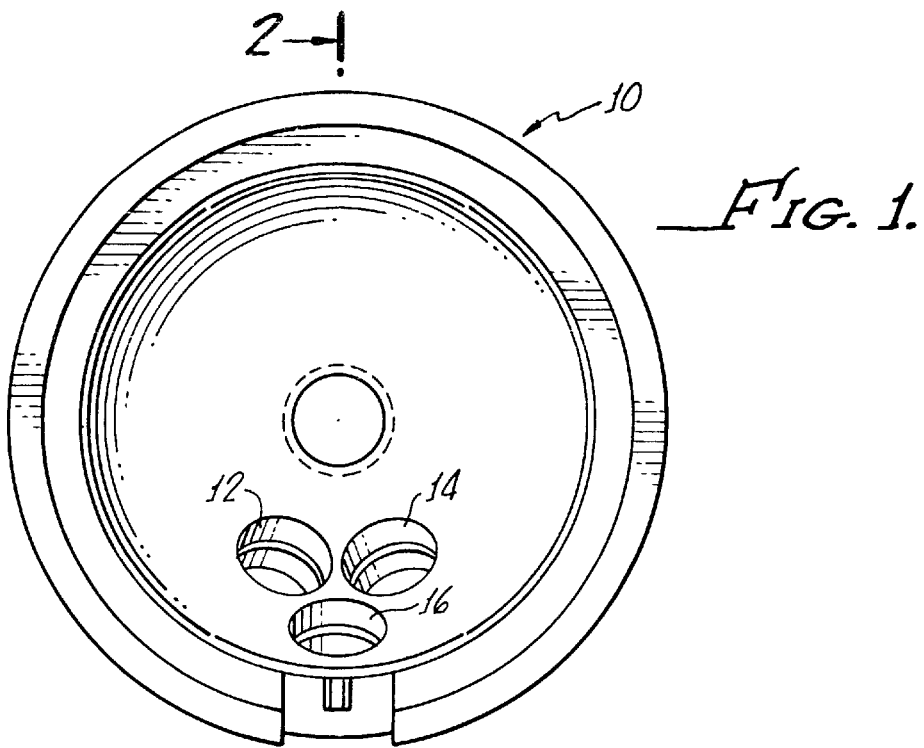
FIG. 1 is a front view of an exemplary embodiment of the acetabular shell of the present invention.

As FIG. 1 shows, the shell 10 has three screw holes 12, 14 and 16. The shell design positions the holes safely in the strongest bone in the superior and posterior acetabulum quadrants. On the other hand, the acetabulum's anterior-inferior quadrants are at risk for drilling and screw placement.

Shell 10 also has a threaded or bayonet locking opening 18 (FIG. 2), which receives an inserter or driver (not shown). The ATH inserter/driver aligns the screw holes in the appropriate quadrant. The shell is then driven into position with approximately a 40° vertical opening and a 15° anteversion angle. After the surgeon checks the shell's position and repositions it if necessary, the surgeon drives the shell home. He or she then removes the inserter/driver.

Before drilling any screw holes, the surgeon must check that the most posterosuperior screw location lies within the desired pelvic bone stock. Most surgeries require use of only one screw hole such as hole 16. Once the position is finalized, the surgeon drills one or more holes through the shell's screw holes. An instrument guide is used for this purpose. The surgeon chooses the proper length and diameter of the drilled holes and then chooses the proper screw. The surgeon must insure that the screw is centered in the shell hole. Also the head of the screw should not protrude above the shell's inner surface, or it will adversely affect the UHMWPE liner's seating.

Once the surgeon finishes tightening the screws, a liner must be chosen. The surgeon make a choice using published data and materials published by the manufacturers of acetabular cups. Before the surgeon locks the liner to the shell, the shell is cleared of all soft tissue and bone and other debris. The liner then is impacted so that it snaps into the shell.

The hole 16 is at a 30° angle from vertical; the other two holes are at about 50°. Normally, only one screw is used, and it uses hole 16. Many patients require no screws to hold the shell in place. Consequently, at least two screw openings normally remain open and UHMWPE from the liner can migrate through the open holes.

Figure 2:
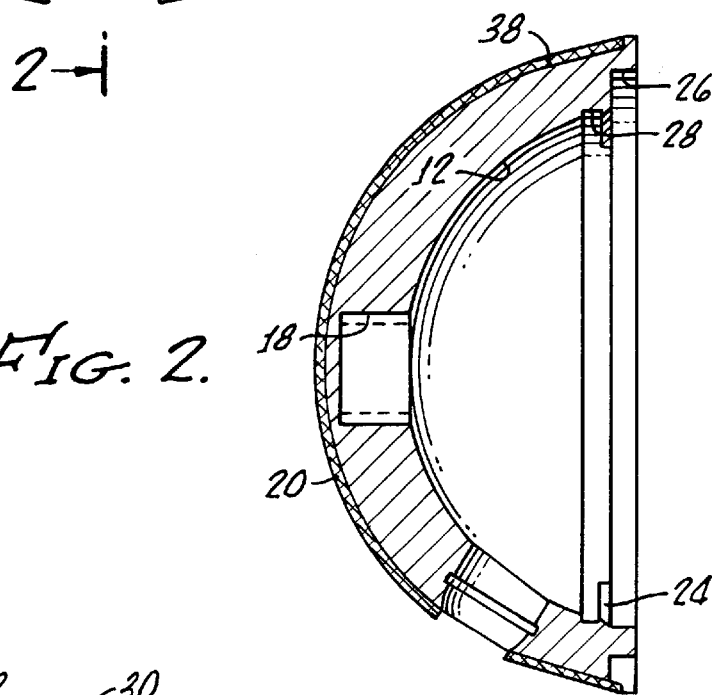
FIG. 2 is a side sectional view of the shell taken through plane 2—2 of FIG. 1.

Shell 10 is formed of a non-corroding titanium alloy Ti6Al-4V per ASTM F136. The outside may be covered with bony ingrowth material 20. The material promotes bone growth around the shell to secure the shell to the bone. Pilliar, U.S. Pat. No. 3,855,638 (1974), describes many of the advantages of porous ingrowth material for securing a prosthesis to bone. The shell receives a UHMWPE liner (not shown). The liner has a curved wall that rests against wall 22 of the shell (FIG. 2). A barbed edge helps secure the liner within the shell. The shell also may have grooves 26 and 28 for receiving corresponding flanges on the liner. The bottom portion 38 of the shell may be flared to 15° to the centerline and tangent to the radius.

Each hole 12, 14 or 16 has a generally cylindrical wall 30 and a curved wall 32. The curvature conforms to that of the head 36 of screw 34. See FIG. 3, which only shows hole 16. Thus, screw 34 secures the shell to the bone (not shown).

Figure 3:
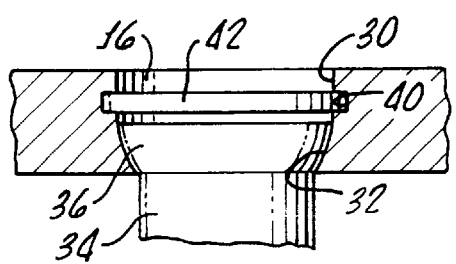
FIG. 3 is a side sectional view of a screw opening.

Each hole 12, 14 or 16 has an annular groove 40 (See FIG. 3, which only shows hole 16). The groove is preferably about 0.03" (0.76 mm (metric conversions are approximate)) thick. The hole's diameter above groove 40 is about 0.314" (8.0 mm). The groove depth is approximately 0.02" (0.5 mm). A UHMWPE disc 42 seats in annular groove 40 for sealing the screw-receiving opening. In the exemplary embodiment, the disc is between 0.020" and 0.025" (0.5 mm and 0.6 mm) thick and between about 0.34" and 0.35" (8.6–9.0 mm) in diameter.

The preferred way to assemble the disc into the hole is to use a rod of a smaller diameter than the hole. For example, if hole 16 is 0.314" (8.0 mm) in diameter, one could use a rod with a 0.25" (6.4 mm) diameter. The surgeon centers the rod on the disc and the hole and then pushes the disc into the hole until it snaps into place. Alternatively, the discs can be added at the factory. The surgeon then would remove the discs from the holes used for a screw.

As FIG. 3 shows, disc 42 seals opening 16 and will prevent debris from migrating through the opening (down in FIG. 3). Because the top of screw head 36 is below the disc, the disc can be used in the hole irrespective of whether a screw is used in any particular hole.

Numerous modifications and alternate embodiments will occur to those skilled in the art. Therefore, applicant intends that the invention be limited only in terms of the appended claims.

We claim:

1. An acetabular shell for receiving an acetabular liner, the acetabular shell comprising a metallic, cup-shaped shell for being attached to bone, a screw-receiving hole through the shell, an annular groove in the screw-receiving hole and a disc received in the annular groove for sealing the screw-receiving hole, the disc having a deformed orientation and a normal orientation, the disc being of a material that is sufficiently flexible that the disc can temporarily deform to the deformed orientation when the disc is being inserted into the screw-receiving hole, the disc returning to the normal orientation when the disc is received in the annular groove.

2. The acetabular shell of claim 1, wherein the acetabular shell has an inside and an outside, the acetabular liner being mounted on the inside of the acetabular shell and wherein when the screw-receiving hole can receive a screw having a top and a screw end, the top of such a screw remaining in a portion of the screw-receiving hole when a screw is inserted in the screw-receiving hole, the annular groove is positioned within the screw-receiving hole such that the disc is adjacent the top of such a screw fastening the acetabular shell to bone.

3. The acetabular shell of claim 1, wherein the disc is formed of ultra-high molecular weight polyethylene.

4. The acetabular shell of claim 1, wherein the hole has a cylindrical region facing the acetabular liner and a screw-securing region facing opposite the acetabular liner, the annular groove being in the cylindrical region.

5. The acetabular shell of claim 4, wherein the screw-securing region tapers to a narrower diameter away from the annular groove.

6. The acetabular shell of claim 1, wherein the disc is between 0.5 mm and 0.6 mm thick.

7. The acetabular shell of claim 6, wherein the groove is about 0.76 mm thick.

8. The acetabular shell of claim 1, wherein the diameter of the groove is between 0.6 mm and 1 mm larger than the diameter of the disc.

\* \* \* \* \*